United States Patent [19]

Knifton

[11] 4,025,547
[45] May 24, 1977

[54] PREPARATION OF ALLYL VINYLACETATE ESTERS

[75] Inventor: John F. Knifton, Poughquag, N.Y.

[73] Assignee: Texaco Inc., New York, N.Y.

[22] Filed: July 17, 1975

[21] Appl. No.: 596,710

[52] U.S. Cl. .................. 260/476 R; 260/410.9 N;
260/468 M; 260/469; 260/486 AC

[51] Int. Cl.$^2$ ........................................ C07C 67/36

[58] Field of Search ........ 260/469, 476 R, 486 AC, 260/410.9 N

[56] References Cited

UNITED STATES PATENTS

| | | | |
|---|---|---|---|
| 3,437,676 | 4/1969 | Kutepow et al. | 260/486 AC |
| 3,700,706 | 10/1972 | Butter | 260/485 R |

OTHER PUBLICATIONS

Tsuji et al., JACS 86, pp. 4350–4353 (1964).
Parshall, Z Naturforsh, 18B, 772 (1963).

*Primary Examiner*—Jane S. Myers
*Attorney, Agent, or Firm*—Thomas H. Whaley; Carl G. Ries; Bernard Marlowe

[57] ABSTRACT

This invention relates to the preparation of allyl vinylacetate esters via the catalytic carbonylation of allylic alcohols. The esters are produced in good yield and selectivity using empirically selected 3-component homogeneous palladium dihalide catalysts consisting essentially of 1) palladium(II) halides stabilized with 2) one or more Group VB donor ligands, and 3) in combination with Group IVB metal halide cocatalysts such as tin(II) halides, tin(IV) halides and germanium(II) halides. An improvement in shorter reaction times, increased yields and selectivity over what has been reported in the literature has been found to be attributable to the use of applicant's catalysts rather than the catalysts used in the art.

8 Claims, No Drawings

PREPARATION OF ALLYL VINYLACETATE ESTERS

SUMMARY OF THE INVENTION

This invention relates broadly to the catalytic carbonylation of allylic alcohols using certain homogeneous 3-component palladium(II) catalysts to prepare allyl vinylacetate esters in good yield and with better than average selectivity.

BACKGROUND OF THE INVENTION

The inventive process, as described therein, may be described by the carbonylation reaction of equation (1) as set forth below:

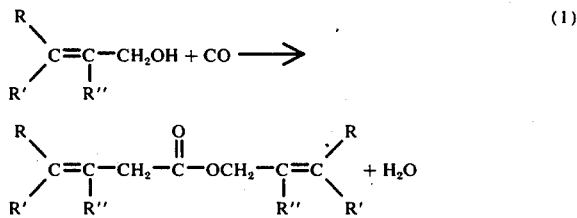

wherein the R, R' and R'' groups of the allylic alcohol substrate may, independently, be alkyl, cycloalkyl, aryl, alkaryl or aralkyl groupings each containing up to 12 carbon atoms, or they may be hydrogen. The reaction is illustrated in Equation 2 by the synthesis of allyl vinylacetate from allyl alcohol. This trifunctional ester is a cross-linking or copolymerizing agent for styrene polymers and its chlorination products are useful as lube oil additives. Further, in addition the di-bromination products are useful fire retardant monomers for fire retardant polymers.

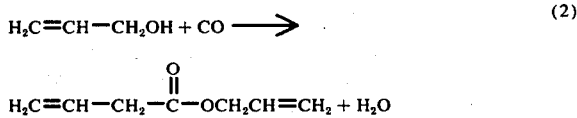

CLOSEST PRIOR ART

The closest prior art is believed to be articles by T. Tsuji et al, J.Amer.Chem.Soc., 86, 4350–4353(1964), and G.W. Parshall, Z Naturforsh, 18B, 772, 1963.

The claims of this application are believed to be distinguishable over the above references in 1) the type of catalyst employed, e.g. simple palladiumm salts, such as $PdCl_2$ described by Tsugi et al, and $Pt[P(p\text{-}FC_6H_4)_3]$, Parshall's platinum fluorine containing catalyst, vs. applicant's ligand-stabilized palladium(II) halide catalyst complexed with excess Group IVB metal halide, i.e. $PdCl_2[P(C_6H_5)_3]_2\text{-}SnCl_2$; 2) much higher molar ratios of allyl alcohol to catalyst metal may be employed; 3) the Art requires much longer reaction times, and 4) lower selectivities are produced in the cited art.

DEFINITIONS

1. Carbonylation — This is the generic term used to describe throughout this disclosure the insertion of carbon monoxide into the carbon-oxygen bond of allylic alcohols (e.g. $CH_2 = CHCH_2OH$) to form allyl vinylacetate esters.

2. Conversion — As defined throughout this disclosure represents the extent of transformation of the allyl alcohol substrate to other products. Conversion is expressed in mole percent and is ordinarily calculated by dividing the amount of the allyl alcohol consumed during the carbonylation by the amount of allyl alcohol charged and multiplying the quotient by 100.

3. Yield — as used herein, represents the efficiency of the empirically selected three(3) component palladium(II) catalyst complexes in carbonylating the allyl alcohol substrate to the corresponding allyl vinyl acetate ester. Yield, like conversion, is expressed as mole percent and is calculated by determining the amount of moles of product formed divided by the total amount of product which can theoretically be formed basis the amount of allyl alcohol charged, and multiplying the quotient obtained by 100.

Analytical procedures used to determine conversions to both the desired and undesired products include standard analytical techniques such as gas chromatography (g.c.), infrared (i.r.) elemental analysis, nuclear magnetic resonance (n.m.r.), among others. Unless otherwise stated, all percentages are mole percent and all temperatures are in centigrade rather than fahrenheit.

Selectivity — as used throughout this specification, refers to efficiency in producing product allyl vinylacetate ester compound to undesired contaminants. Selectivity is calculated by determining the mole percent of product ester formed divided by the mole percent of allyl alcohol consumed, multiplied by 100.

HOMOGENEOUS PALLADIUM CATALYSTS

The homogeneous palladium catalyst of this invention consists of at least three components: 1) a palladium(II) halide selected from the group consisting of palladium(II) chloride, palladium(II) bromide and palladium(II) iodide complexed with 2) one or more Group VB donor ligands, and in combination with 3) a Group IVB metal halide co-catalyst.

Each Group VB donor ligand contains one or more donor atoms selected from Group VB of the Periodic Chart of the Elements (Advanced Inorganic Chemistry by F.A. Cotton and G. Wilkinson, 2nd Ed., 1966), preferably it contains one or more trivalent phosphorus or arsenic atoms. These Group VB donor atoms are bonded to hydrocarbyl radicals selected from the group consisting of aryl, alkyl, and substituted aryl radicals, which may contain up to 20 carbon atoms and need not be the same.

Illustrative of suitable Group VB donor ligands which may be used in combination with the palladium(II) halide and the Group IVB metal halide to form active carbonylation catalysts for the preparation of allyl vinylacetate esters are:

$P(C_6H_5)_3$, $As(C_6H_5)_3$, $P(CH_3)_2(C_6H_5)$, $P(p\text{-}CH_3\cdot C_6H_4)_3$, $P(pCl\cdot C_6H_4)_3$, $P(o\text{-}CH_3O\cdot C_6H_4)_3$, $P(p\text{-}CH_3O\cdot C_6H_4)_3$, $P(OC_6H_5)_3$, $P(C_6H_{11})_3$, $As(n\text{-}C_4H_9)_3$, $P[(p\text{-}CH_3\cdot C_6H_4)(C_6H_5)_2]$, $(C_6H_5)_2P(CH_2)_2P(C_6H_5)_2$, $(C_6H_5)_2P(CH_2)P(C_6H_5)_2$, and $Sb(C_6H_5)_3$.

The Group IVB metal halides that may be used as co-catalysts in this invention include the halides of tin(II), tin(IV) and germanium(II). Illustrative examples include tin(II) chloride, tin(IV) chloride, tin(II) bromide and germanium(II) chloride. In certain cases, the anhydrous chlorides of the Group IVB metal halides are favored, with anhydrous tin(II) chloride being the preferred co-catalyst.

The following complexes are among the many ligand-stabilized palladium(II)-Group IVB metal halide complexes which can be used in the catalytic conversion of allylic alcohol substrates to allyl vinylacetate esters:

$PdCl_2[P(C_6H_5)_3]_2$-$SnCl_2$, $PdCl_2[As(C_6H_5)_3]_2$-$SnCl_2$, $PdCl_2[P(OC_6H_5)_3]_2$, $PdCl_2[P(p\text{-}CH_3O\cdot C_6H_4)_3]_2$-$SnCl_2$, $PdCl_2[P(C_6H_5)_3]_2$-$GeCl_2$, $PdCl_2[P(p\text{-}Cl\cdot C_6H_5)_3]_2$-$SnCl_2$, $PdCl_2[P(p\text{-}CH_3\cdot C_6H_4)_3]_2$-$SnCl_2$, $PdCl_2[P(C_6H_5)_3]_2$-$SnCl_4$, and $PdCl_2[P(CH_3)_2C_6H_5]_2$-$SnCl_2$.

In certain cases the Group VB donor ligand, typified by triphenylphosphine, may be used in excess of the amount required for complex formation, and the Group IVB metal halide co-catalyst also in excess in order to obtain a stable and active catalyst.

The homogeneous catalyst complexes described supra are known in the literature, although not for these purposes, and methods for their preparation have been described in the literature*. While many of these three component catalysts have been disclosed previously to function as hydroformylation and carboxylation catalysts for various aliphatic olefins, insofar as is known the carbonylation of allylic alcohol substrates to allyl vinylacetate esters under the claimed conditions is novel.

*H. Itatani and J.C.Bailar, J.Amer.Oil Chem. Soc., 44, 147(1967)

Advantages of these three component homogeneous palladium catalysts over the prior art include:

1. The ability to carbonylate allyl alcohols to the corresponding allyl vinylacetate esters below the isomerization temperature of the allyl substrate, that is at temperatures below 160° to 200° C, the operational range of many of the prior art catalysts that are used for carbonylation.
2. The ability to selectively carbonylate said allyl alcohol to the desired allyl-vinylacetate products, with little or no production of the undesirable by-products, and
3. The ability to consistently prepare allyl vinylacetate in a one-step process in almost twice the yield of the known art.

ALLYLIC ALCOHOL SUBSTRATES

As used throughout this disclosure, this term refers to a class of unsaturated allylic alcohols containing 3 to 30 carbon atoms and having the general structure:

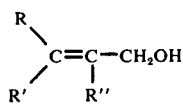

wherein the unsaturated, double bond is between carbon-carbon atoms, and R, R' and R'' may independently be hydrogen, or alkyl, aryl cycloalkyl, alkaryl or aralkyl groupings each containing up to 12 carbon atoms. Suitable allylic alcohol substrates include allyl alcohol, 2-methylallyl alcohol, crotyl alcohol, 2-pentenyl alcohol, 2-methyl-2-butenyl alcohol, 2-hexenyl alcohol, 3-methyl-2-pententyl alcohol, 4-propyl-2-pentenyl alcohol, cinnamyl alcohol, and naturally occurring unsaturated alcohols such as geraniol, nerol, farnesol and phytol*.

*"Organic Chemistry" by I.L. Finar, Longmans, London, Vol. I, p. 256

Alternatively, in an extension of this invention, the unsaturated carbon-carbon bond of the alcohol substrate may be an acetylenic, triple bond. Illustrative examples of suitable unsaturated alcohol substrates containing triple bonds include propargyl alcohol, 3-methylpropargyl alcohol and 3-ethylpropargyl alcohol.

REACTION PARAMETERS FOR CARBONYLATION OF ALLYL ALCOHOL

I. Temperatures and Pressures

The temperature and pressure ranges which can be employed for ester formation are variables dependent upon other experimental factors including the substrate allyl alcohol employed, the concentration and particular choice of catalyst, the presence or absence of added solvent, and the time of reaction among other things. Using allyl alcohol as a typical unsaturated alkanol substrate and $PdCl_2[P(C_6H_5)_3]_2$-$SnCl_2$ as a representative catalyst, the range of operability is from about 20° to at least 120° C when superatmospheric pressures of 100–5000 psig or higher are employed.

II. Molar ratio of palladium catalyst to allyl alcohol substrate

Experimental work indicates that a molar ratio of at least $5 \times 10^4$ moles of allyl alcohol per mole of homogeneous palladium catalyst complex can be employed in most instances. Much lower ratios (e.g. 25 moles of substrate per mole of palladium catalyst) are not harmful but are economically unattractive.

III. Reaction Times required

As previously indicated in the analogous discussion on temperatures and pressures required in the reaction, experimental variables are important in arriving at reaction times. Generally substantial conversions (70% or higher) of the substrates to the desired unsaturated alcohol product can almost always be accomplished within 20 hours with 4 to 8 hours representing the more usual reaction time interval.

IV. Inert Solvents

While inert solvents are not necessary for the carbonylation of allylic alcohols, they may be employed in certain circumstances to improve the solubility of the homogeneous palladium catalyst. Suitable inert solvents include aromatics such as benzene, toluene and xylenes, ethers such as 1,2-dimethyoxyethane, and p-dioxane, ketones such as diethyl ketone and methyl isobutyl ketone, and paraffins such as n-hexanes, n-heptanes and petroleum ethers.

PROCESS SEQUENCE AND VARIATIONS

Carbonylation

In general, the components of the carbonylation mixture, including optional inert solvent, allylic alcohol and homogeneous, ligand-stabilized palladium(II) dihalide-Group IVB metal catalyst complex, may be added in any sequence as long as good agitation of the reaction mixture and freedom from oxidizing agents or an oxidizing atmosphere is provided. Process variations which can be employed include:

1. The homogeneous catalyst may be preformed in an inert environment and added preformed to deoxygenated inert solvent prior to the carbonylation of the allyl alcohol.
2. Preferably, to minimize stability problems, it is recommended that the catalyst complexes be formed in situ by mixing the deoxygenated inert solvent and allyl alcohol, followed by the addition of excess Group IVB metal halide, and finally by the addition of the ligand-stabilized palladium(II) halide, such as $PdCl_2[P(C_6H_5)_3]_2$, to form the reaction mixture.

3. After employing variation 1) or 2) the reaction mixture of allylic alkanol, inert solvent, ligand-stabilized palladium(II) halide complex and excess Group IVB metal halide, lacking only carbon monoxide, is sealed and pressurized using carbon monoxide and/or inert gas, initially only to low pressures ranging from about 10 psig to about 100 psig. After a homogeneous mixture is obtained, sufficient carbon monoxide is introduced to at least satisfy the stoichiometry needed for the preparation of the allyl vinylacetate ester, and to increase the superatmospheric pressure of the system up to about 1000 psig to 3000 psig. The pressurized reaction mixture is then heated until experience, based upon prior analysis, indicates that the desired carbonylation of the allyl alcohol has been obtained.

In order to describe the claimed invention in the greatest possible detail, the following illustrative examples are submitted. It should be noted that unless otherwise stated, all parts are by weight and all temperatures are by centigrade. Further, in all preparations the reaction mixtures are degassed by passing nitrogen or noble gases through the mixture before it is utilized.

The term "substantially free of water" refers to solutions containing 2% or less water as determined by the Karl Fischer titration.

EXAMPLE 1

SYNTHESIS OF ALLYL VINYLACETATE FROM ALLYL ALCOHOL CATALYZED BY BIS(TRIPHENYLPHOSPHINE) PALLADIUM(II) CHLORIDE-TIN(II) CHLORIDE

A. To a deoxygenated, substantially water-free, mixture of benzene (75 ml) and allyl alcohol (100 mmole, 6.80 ml) contained in an appropriately sized, glass-lined pressure reactor, fitted with means of agitating (or stirring), sampling, heating, cooling and pressurizing, is charged under a nitrogen purge with stirring, 0.96 g of tin(II) chloride, (5.0 mmole) and 0.35 g of $PdCl_2[P(C_6H_5)_3]_2$ complex (0.5 mmole). Stirring is continued for 2-5 minutes to give a clear, yellow solution with little residual solids. The charged glass-liner reactor is flushed with nitrogen, sealed, pressurized with CO to 3000 psig, and the sealed reactor heated to 80° C. The reactor is held at 80° C with rocking for 6 hours and cooled. Sixty-five g of pale yellow liquid is recovered and analysis by gas chromatography shows conversion of allyl alcohol > 98%. Distillation under reduced pressure (1 cm) produced a fraction which was worked-up to give 5.55 g of allyl vinylacetate product (Yield 88 mole %)

B. In this run the same catalyst and reactants are employed except that the catalyst is synthesized then added preformed to the reaction mixture. No significant discernable difference in conversion, yield and selectivity is seen.

EXAMPLES 2-6

SYNTHESIS OF ALLYL VINYL ACETATE USING ALTERNATIVE INERT AROMATIC SOLVENTS

In these examples, the conditions of Example 1 are substantially duplicated, except that 75 ml of the designated inert aromatic solvent is substituted for benzene using the same $PdCl_2[P(C_6H_5)_3]_2$ complex with a 10 molar excess of $SnCl_2$ as the catalyst formed in situ.

Yields of allyl vinylacetate are in the 40–90 mole % range for the following aromatic solvents:

| Example | Solvent |
|---|---|
| 2 | Toluene |
| 3 | O-Xylene |
| 4 | p-Xylene |
| 5 | Mesitylene |
| 6 | Ethyl Benzene |

SYNTHESIS OF ALLYL VINYLACETATE IN THE ABSENCE OF INERT SOLVENT

To a deoxygenated, substantially water-free sample of allyl alcohol (68 ml, 1 mole) contained in the glass-liner pressure reactor of Example 1(A) is charged, under a nitrogen purge with stirring, 0.96 g of tin(II) chloride (5.0 mmole) and 0.35 g of $PdCl_2[P(C_6H_5)_3]_2$ (0.5 mmole). Stirring is continued for 2–5 minutes. The reactor is flushed and pressurized with CO to 2000 psig and the sealed reactor heated to 80° C for 12 hours. On cooling, 59.0 g of reddish-brown liquid is recovered. Distillation under reduced pressure (2–5 mm) produces an allyl vinylacetate fraction (9.4 gm) with purity greater than 98% (Yield 0.075 mole).

EXAMPLE 8

SYNTHESIS OF ALLYL VINYLACETATE FROM ALLYL ALCOHOL CATALYZED BY BIS(TRI-p-TOLYLPHOSPHINE)(PALLADIUM(II)-TIN(II) CHLORIDE

Using the procedure, equipment, proportions and reaction parameters employed in Example 1, $PdCl_2[P(p-CH_3\cdot C_6H_4)_3]_2\text{-}SnCl_2$ is substituted for the homogeneous palladium complex of Example 1 on a mole per mole basis. At the end of the reaction time the pressurized reactor is cooled, vented, and the liquid product analyzed by gas chromatography. Conversion of the allyl alcohol charged is 59%, allyl vinylacetate is obtained in 46 mole % yield.

EXAMPLE 9

SYNTHESIS OF ALLYL VINYLACETATE FROM ALLYL ALCOHOL CATALYZED BY BIS(TRIPHENYLPHOSPHINE) GERMANIUM(II) CHLORIDE

A. Using the procedure, equipment, and proportions employed in Example 1, $PdCl_2[P(C_6H_5)_3]_2\text{-}GeCl_2$ is substituted for the homogeneous palladium complex of Example 1 on a mole per mole basis. Carbonylation of the allyl alcohol is carried out under 2000 psig of CO. At the end of the reaction time the pressurized reactor is cooled, vented and the liquid product analyzed by gas chromatography. Allyl vinylacetate is obtained in 67 mole % yield.

B. In this run the same catalyst and reactants are employed except that the carbonylation is carried out under 1000 psig of CO. Allyl vinylacetate is again the major product.

EXAMPLES 10 to 14

SYNTHESIS OF ALLYL VINYLACETATE USING OTHER LIGAND-STABILIZED PALLADIUM(II) HALIDE - GROUP IVB METAL HALIDE CATALYST COMPLEXES

In these examples the carbonylation of allyl alcohol to allyl vinylacetate was carried out in accordance with the procedure outlined in Example 1, but in the presence of various other ligand-stabilized palladium(II) halide — Group IVB metal halide complexes. The following palladium(II) complexes showed satisfactory performance:

| Example | Palladium Complex |
|---|---|
| 10 | $PdCl_2[As(C_6H_5)_3]_2\text{-}SnCl_2$ |
| 11 | $PdCl_2[P(p\text{-}CH_3O\cdot C_6H_4)_3]_2\text{-}SnCl_2$ |
| 12 | $PdCl_2[P(p\text{-}Cl\cdot C_6H_4)_3]_2\text{-}SnCl_2$ |
| 13 | $PdCl_2[P(CH_3)_2C_6H_5]_2\text{-}SnCl_2$ |
| 14 | $PdCl_2[P(C_6H_5)_3]_2\text{-}SnCl_4$ |

EXAMPLES 15 to 18

SYNTHESIS OF ALLYL VINYLACETATE UNDER VARIOUS TEMPERATURE CONDITIONS

In these Examples the procedure, reactants and catalyst of Example 1(A) is followed except that the reaction temperature is varied between 20° and 120° C to determine operability and optimum parameters of temperature while holding the other variables constant. Table I indicates that the process is operable between about 20° and 120° C using the favored catalyst, $PdCl_2[P(C_6H_5)_3]_2\text{-}lOSnCl_2$.

TABLE I

| EXAMPLE | TEMPERATURE (°C) | ALLYL ALCOHOL CONV. (%) | ALLYL VINYLACETATE YIELD (MOLE %) |
|---|---|---|---|
| 15 | 20 | 61 | 53 |
| 16 | 60 | >98 | 84 |
| 17 | 80 | >98 | 88 |
| 18 | 120 | 80 | 62 |

EXAMPLES 19 to 22

SYNTHESIS OF OTHER ALLYL VINYLACETATE ESTERS

In these examples various allyl alcohol derivatives are carbonylated to allyl vinylacetate esters using the palladium homogeneous catalyst complex $PdCl_2[P(C_6H_5)_3]_2\text{-}SnCl_2$ and the procedure of Example 1A. It may be seen from the data in Table II that under the specified conditions both alkyl and aryl substituted allyl alcohols may be readily carbonylated to the corresponding allyl vinylacetate esters by this technique.

TABLE II[a]

| EX. | ALLYL ALCOHOL | ALLYL ALCOHOL CONVERSION (%) | ALLYL VINYLACETATE ESTER PRODUCT IDENTITY | YIELD (MOLE %) |
|---|---|---|---|---|
| 19 | 2-Methylallyl Alcohol $CH_2=\overset{\underset{\mid}{CH_3}}{C}-CH_2OH$ | 55[b] | 2-Methylallyl 3-Methylvinylacetate $CH_2=\overset{\underset{\mid}{CH_3}}{C}-CH_2-O-\overset{\underset{\|}{O}}{C}-CH_2-\overset{\underset{\mid}{CH_3}}{C}=CH_2$ | 55 |
| 20 | Crotyl Alcohol $CH_3-CH=CH-CH_2OH$ | >98 | Crotyl 4-Methylvinylacetate $CH_3-CH=CH-CH_2-O-\overset{\underset{\|}{O}}{C}-CH_2-CH=CH-CH_3$ | 90 |
| 21 | 2-Hexenyl Alcohol $CH_3\cdot(CH_2)_2\cdot CH=CH-CH_2OH$ | 95 | 2-Hexenyl 4-Propylvinylacetate $CH_3-(CH_2)_2-CH=CH-CH_2-O-\overset{\underset{\|}{O}}{C}-CH_2-CH=CH-(CH_2)_2-CH_3$ | 80 |
| 22 | Cinnamyl Alcohol $C_6H_5CH=CH-CH_2OH$ | 60[c] | Cinnamyl 4-Phenylvinylacetate $C_6H_5CH=CH-CH_2-O-\overset{\underset{\|}{O}}{C}-CH_2-CH=CHC_6H_5$ | 30 |

[a]Run Conditions: Initial (Alcohol)/[Pd] = 200; 80° C; 2000 psig CO; 360 Min; Solvent, Benzene
[b]Run in Toluene
[c]After 120 min.

As the several examples and previous discussion indicate, both process aspects of this invention are novel and advantageous. For example, the closest known carbonylation of allyl alcohol using $PdCl_2$ as catalyst produces only about 40% yield of allyl vinylacetate while the instant catalysts are capable of producing about twice the yield of the art.

Further, applicant's novel carbonylation may be carried out with a variety of allylic alcohol substrates to give allyl vinylacetate esters in fairly good yields and under moderate parameters of time, temperature and pressure.

Other advantages and applications of the invention concepts will become apparent to those skilled in the art after a perusal of the claims which follow in view of the specification.

What is claimed is:

1. A process for converting allylic alcohol substrates containing 3 to 30 carbon atoms, said alcohol substrates being selected from the group consisting of: allyl alcohol, 2-methylallyl alcohol, crotyl alcohol, 2-pentenyl alcohol, 2-metyl-2-butenyl alcohol, 2-hexenyl alcohol, 3-methyl-2-pentenyl alcohol, 4-propyl-2-pentenyl alcohol, cinnamyl alcohol, geraniol, nerol, farnesol and phytol to linear allyl vinyl vinylacetate esters in good yields by a process of:

a. Admixing each mole of allylic alcohol to be carbonylated to said allyl vinylacetate ester with at least a catalytic amount of a ligand-stabilized palladium(II) halide-Group IVB metal halide catalyst selected from the group consisting of:

$PdCl_2[P(C_6H_5)_3]_2\text{-}SnCl_2$, $PdCl_2[P(C_6H_5)_3]_2\text{-}GeCl_2$, $PdCl_2[P(p\text{-}CH_3\cdot C_6H_4)_3]_2\text{-}SnCl_2$, $PdCl_2[P(p\text{-}Cl\cdot C_6H_4)_3]_2\text{-}SnCl_2$, $PdCl_2[P(p\text{-}CH_3\cdot C_6H_4)_3]_2\text{-}SnCl_2$, $PdCl_2[P(CH_3)_2C_6H_5]_2\text{-}SnCl_2$, $PdCl_2[P(C_6H_5)_3]_2\text{-}SnCl_4$, and $PdCl_2[As(C_6H_5)_3]_2\text{-}SnCl_2$;

b. Pressurizing said reaction mixture with sufficient carbon monoxide to satisfy the stoichiometry of the carbonylation reaction;

c. Heating said pressurized reaction mixture to between 20° and 120° C until conversion of the allylic alcohol substrate to said allyl vinylacetate ester takes place, and d. Isolating said allyl vinylacetate contained therein.

2. The process of claim 1 wherein said homogeneous palladium catalyst is prepared in situ by adding as separate components the ligand-stabilized palladium(II) halide salt and the Group IVB halide.

3. The process of claim 1 wherein said homogeneous palladium catalyst is prepared pre-formed before adding to the allylic alcohol substrate.

4. The process of claim 1 wherein said allylic alcohol carhonylation is carried out in the presence of an inert solvent.

5. The process of claim 4 wherein said inert solvent is an aromatic solvent selected from the group consisting of benzene, toluene and xylenes.

6. The process of claim 1 wherein said allylic alcohol substrate is allyl alcohol and the product ester is allyl vinylacetate.

7. The process of claim 1 wherein said allylic alcohol substrate is crotyl alcohol and the product ester is crotyl 4-methylvinylacetate.

8. The process of claim 1 wherein said allylic alcohol substrate is cinnamyl alcohol and the product ester is cinnamyl 4-phenylvinylacetate.

* * * * *